US010973620B2

(12) United States Patent
Choi et al.

(10) Patent No.: US 10,973,620 B2
(45) Date of Patent: Apr. 13, 2021

(54) BIOMIMETIC ARTIFICIAL MUSCLE MODULE, BIOMIMETIC ARTIFICIAL MUSCLE ASSEMBLY HAVING THE SAME, AND METHOD OF CONTROLLING THE SAME

(71) Applicant: KOREA INSTITUTE OF MACHINERY & MATERIALS, Daejeon (KR)

(72) Inventors: Sang-Kyu Choi, Daejeon (KR); Hyun Joon Kwon, Odenton, MD (US); Jae Keun Shim, Clarksville, MD (US); Young-Su Son, Daejeon (KR); Cheol-hoon Park, Daejeon (KR); Seyoung Kim, Anyang-si (KR)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 69 days.

(21) Appl. No.: 16/264,183

(22) Filed: Jan. 31, 2019

(65) Prior Publication Data

US 2020/0246129 A1   Aug. 6, 2020

(51) Int. Cl.
*A61F 2/08*       (2006.01)
*G01L 5/10*       (2020.01)
(Continued)

(52) U.S. Cl.
CPC .............. *A61F 2/08* (2013.01); *G01B 7/02* (2013.01); *G01L 5/10* (2013.01); *G01P 3/42* (2013.01);
(Continued)

(58) Field of Classification Search
CPC ............... A61F 2/08; A61F 2002/0894; A61F 2002/487; A61F 2002/5066;
(Continued)

(56) References Cited

U.S. PATENT DOCUMENTS 9,463,085 B1 * 10/2016 Theobald .................. A61F 2/54
2014/0371854 A1 * 12/2014 Engin ....................... A61F 2/08
623/14.13
(Continued)

FOREIGN PATENT DOCUMENTS

KR       10-1731163 B1     4/2017
KR       10-1795782 B1    11/2017

*Primary Examiner* — Suba Ganesan
*Assistant Examiner* — Aren Patel
(74) *Attorney, Agent, or Firm* — Hauptman Ham, LLP

(57) ABSTRACT

In a biomimetic artificial muscle module, a biomimetic artificial muscle assembly having the biomimetic artificial muscle module, and a method of controlling the biomimetic artificial muscle module, the biomimetic artificial muscle module includes an operating part, an elastic part, a driving part, a locking part and first and second sensors. The operating part contracts or relaxes along a longitudinal direction. The elastic part is connected to a first end of the operating part, and behaves elastically behave according to an external force. The driving part is connected to a second end of the operating part, and drives the operating part to be contracted or relaxed. The locking part selectively blocks a length of the operating part from being changed. The first and second sensors respectively sense the elastic part and the operating part.

20 Claims, 15 Drawing Sheets

(51) Int. Cl.
  *G01B 7/02* (2006.01)
  *G01P 3/42* (2006.01)
  *G01P 15/00* (2006.01)
  *A61F 2/48* (2006.01)

(52) U.S. Cl.
  CPC ...... *G01P 15/00* (2013.01); *A61F 2002/0894* (2013.01); *A61F 2002/482* (2013.01); *A61F 2002/487* (2013.01); *A61F 2210/0014* (2013.01); *A61F 2210/0057* (2013.01); *A61F 2250/0007* (2013.01)

(58) Field of Classification Search
  CPC ..... A61F 2210/0014; A61F 2210/0057; G01B 7/02; G01L 5/10; G01P 3/42; G01P 15/00
  USPC ..................................................... 623/14.13
  See application file for complete search history.

(56) References Cited

U.S. PATENT DOCUMENTS

| | | | |
|---|---|---|---|
| 2016/0184082 A1* | 6/2016 | Lizzio | H01F 7/066 623/14.13 |
| 2016/0206420 A1* | 7/2016 | Yun | A61F 2/08 |

* cited by examiner

BIOMIMETIC ARTIFICIAL MUSCLE MODULE, BIOMIMETIC ARTIFICIAL MUSCLE ASSEMBLY HAVING THE SAME, AND METHOD OF CONTROLLING THE SAME

BACKGROUND

1. Field of Disclosure

The present disclosure of invention relates to a biomimetic artificial muscle module, a biomimetic artificial muscle assembly having the biomimetic artificial muscle module, and a method of controlling the biomimetic artificial muscle module, and more specifically the present disclosure of invention relates to a biomimetic artificial muscle module, a biomimetic artificial muscle assembly having the biomimetic artificial muscle module, and a method of controlling the biomimetic artificial muscle module, capable of mimicking a structure of the muscle-tendon unit in human beings to substantially reproduce biological characteristics of muscle-tendon contraction based on human motor control mechanism.

2. Description of Related Technology

To substitute for the damaged human muscle, to strengthen or support muscular strength, artificial muscle or biomimetic robot has been developed.

However, in the conventional artificial muscle or the conventional biomimetic robot, a rotational operator disposed at a joint is used to mimic the operation of the joint, but the output of the rotational operator is relatively low and the energy efficiency is relatively low, and thus an operation for automatic motion may be limited.

Thus, recently to solve the above-mentioned problem, a linear operator mimicking a biological form or function of the human beings or an animals has been developed, but until now, in the linear operator, biological muscle-tendon contraction mechanism is not applied in the points of the structure, the function and the control of the linear operator, and thus, the linear operator does not perform the biological characteristics of the muscle-tendon contraction such as isometric contraction, isotonic contraction and elastic contraction.

For example, Korean Patent Number 10-1731163 merely discloses that an artificial muscle operator mimicking contraction or expansion of the muscle of human beings, and Koran Patent Number 10-1795782 merely discloses that an artificial muscle module supporting the motion or muscle strength using a muscle tube expanded by an air inlet. However, in the prior arts, biological muscle-tendon contraction mechanism is not applied in the above-mentioned muscle operator or the muscle module specially in the points of the structure, the function and the control thereof, and thus the biological characteristics of the muscle-tendon contraction such as isometric contraction, isotonic contraction and elastic contraction are not performed.

SUMMARY

The present invention is developed to solve the above-mentioned problems of the related arts. The present invention provides a biomimetic artificial muscle module capable of mimicking the biological muscle-tendon contraction such as isometric, isotonic and elastic contraction more correctly, based on a form, a function and a control of a muscle-tendon unit in human beings or animals, so that the control may be simplified with enhanced movement performance and minimized energy consumption, to perform minimization or modularization.

In addition, the present invention also provides a biomimetic artificial muscle assembly having the biomimetic artificial muscle module.

In addition, the present invention also provides a method of controlling the biomimetic artificial module and the biomimetic artificial muscle assembly.

According to an example embodiment, the biomimetic artificial muscle module includes an operating part, an elastic part, a driving part, a locking part and first and second sensors. The operating part contracts or relaxes along a longitudinal direction. The elastic part is connected to a first end of the operating part, and behaves elastically behave according to an external force. The driving part is connected to a second end of the operating part, and drives the operating part to be contracted or relaxed. The locking part selectively blocks a length of the operating part from being changed. The first and second sensors respectively sense the elastic part and the operating part.

In an example, the biomimetic artificial muscle module may further include a driving transmitting part transmitting the driving of the driving part to the operating part.

In an example, the biomimetic artificial muscle module may further include a first connector connecting the elastic part with the operating part, and a second connector connecting the operating part with the driving transmitting part.

In an example, the driving part, the operating part, the driving transmitting part and the second connector may be integrally formed with each other.

In an example, the biomimetic artificial muscle module may further include an outer part forming an outer structure of the artificial muscle module, and a cover enclosing elements inside of the outer part, and connecting the elements to outer elements.

In an example, the first sensor may measure a length or a tension of the elastic part, and the second sensor may measure driving amount of the driving part and/or a length or a tension of the operating part to calculate driving amount, a length, a tension, a velocity and an acceleration of the artificial muscle module.

In an example, the elastic part may be one of a spring, an elastic rubber and an elastic wire.

In an example, the operating part may be one of shape-memory alloys, a twisting wire/fiber and a thermal contraction tube.

In an example, the driving part may be driven via one of pneumatic driving, electric field driving, thermal driving and mechanical driving.

In an example, the locking part may block the driving part and the operating part from being operated to minimize energy consumption, when elastic behavior of the muscle-tendon unit is unnecessary to be considered.

In an example, in mimicking isometric contraction, a length of the elastic part may be increased or decreased, a length of the operating part may be decreased or increased, and thus total length of the artificial muscle module may be maintained.

In an example, in mimicking isotonic contraction, a length of the elastic part may be maintained, a length of the operating part may be decreased or increased, and thus total length of the artificial muscle module may be decreased or increased.

In an example, in mimicking elastic contraction, a length of the elastic part may be decreased or increased, a length of the operating part may be decreased o increased, and thus total length of the artificial muscle module may be decreased or increased due to the sum of length change of the elastic part and the operating part.

According to another example embodiment, a method of controlling a biomimetic artificial muscle module includes elastically behaving an elastic part selectively according to an external force, selectively driving an operating part connected to a first end of the elastic part, by a driving part, selectively contracting or relaxing the operating part driven by the driving part both feed-forward and feedback manner depending on a task to control an original length of an operating part, and blocking the driving part and the operating part from being operated, by the locking part disposed adjacent to the driving part.

According to still another example embodiment, an artificial muscle assembly includes an artificial muscle elastic module and an artificial muscle operating module. The artificial muscle elastic module includes an elastic part connected to a first end of an operating part, and elastically behaving according to an external force, and a first sensor sensing the elastic part. The artificial muscle operating module includes an operating part contracting or relaxing along a longitudinal direction, a driving part connected to a second end of the operating part, and driving the operating part to be contracted or relaxed, a locking part selectively blocking a length of the operating part from being changed, and a second sensor sensing the operating part or the driving part.

In an example, a plurality of the artificial muscle elastic modules may be connected, continuously in series, in parallel with each other, or serially and in parallel. A plurality of the artificial muscle operating modules may be connected, continuously in series, in parallel with each other, or serially and in parallel. The artificial muscle elastic module may be connected to at least one artificial muscle operating modules.

In an example, an outer part and a cover may be formed at each of the artificial muscle elastic module and the artificial muscle operating module.

In an example, the locking part may block the driving part and the operating part from being operated to minimize energy consumption, when elastic behavior of the muscle-tendon unit is unnecessary to be considered.

In an example, in mimicking isometric contraction, a length of the artificial muscle elastic module may be increased or decreased, a length of the artificial muscle operating module may be decreased or increased, and thus total length of the artificial muscle assembly may be maintained.

In an example, in mimicking isotonic contraction, a length of the artificial muscle elastic module may be maintained, a length of the artificial muscle operating module may be decreased or increased, and thus total length of the artificial muscle assembly may be decreased or increased.

In an example, in mimicking elastic contraction, a length of the artificial muscle elastic module may be decreased or increased, a length of the artificial muscle operating module may be decreased or increased, and thus total length of the artificial muscle assembly may be decreased or increased due to the sum of length change of the artificial muscle elastic module and the artificial muscle operating module.

According to still another example embodiment, a method of controlling an artificial muscle assembly includes elastically behaving an artificial muscle elastic module selectively according to an external force, selectively driving an artificial muscle operating module connected to a first end of an elastic part, by a driving part of the artificial muscle operating module, selectively contracting or relaxing the artificial muscle operating module driven by the driving part, and blocking the artificial muscle operating module from being operated, by a locking part disposed adjacent to the driving part both feed-forward and feedback manner depending on a task to control an original length of an operating part.

According to the present example embodiments, biological characteristics of muscle-tendon contraction in human beings or animals may be easily mimicked with relatively simple structure and control method.

The operating part is merely controlled to be contracted or relaxed, such that the motion of muscle-tendon unit may be mimicked. Thus, the control may be simplified for the simulation more correctly.

In addition, since the biomimetic artificial muscle module includes only a few components with simple structure, miniaturization and modularization may be achieved and thus may be applied to various applications.

In addition, various kinds of materials, structures, and designs may be applied to the elastic part, and various kinds of mechanism, structures, functions and designs may be applied to the driving part and the operating part.

In addition, due to the capability of miniaturization and modularization, the biomimetic artificial muscle assembly having a plurality of modules may be constructed, so that the various shapes of muscle-tendon unit and its functional characteristics in human beings may be mimicked more precisely.

In addition, the biomimetic artificial muscle module and biomimetic artificial muscle assembly may mimic the contraction characteristics of human or animal muscle-tendon unit more correctly and effectively by its design and control method.

DETAILED DESCRIPTION

Figure 1A:
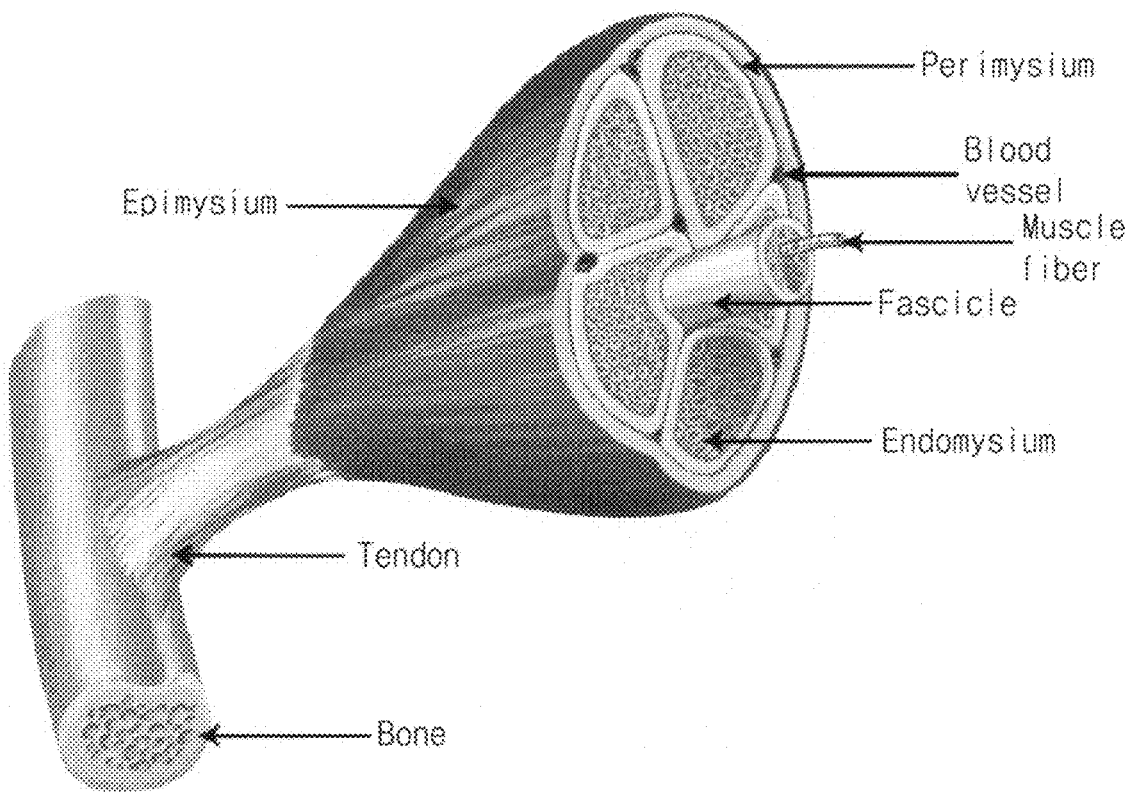
FIG. 1A is a schematic view illustrating a muscle-tendon unit in human beings or animals.

The invention is described more fully hereinafter with Reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention.

As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

In addition, the same reference numerals will be used to refer to the same or like parts and any further repetitive explanation concerning the above elements will be omitted. Detailed explanation regarding prior arts will be omitted not to increase uncertainty of the present example embodiments of the present invention.

Hereinafter, the embodiments of the present invention will be described in detail with reference to the accompanied drawings.

Referring to FIGS. 1A to 4, a structure of a muscle-tendon unit and biological characteristics of muscle-tendon contraction in human beings or animals, are explained first, before explaining a biomimetic artificial muscle module, a biomimetic artificial muscle assembly having the biomimetic artificial muscle module, according to the present example embodiments.

Figure 1B:
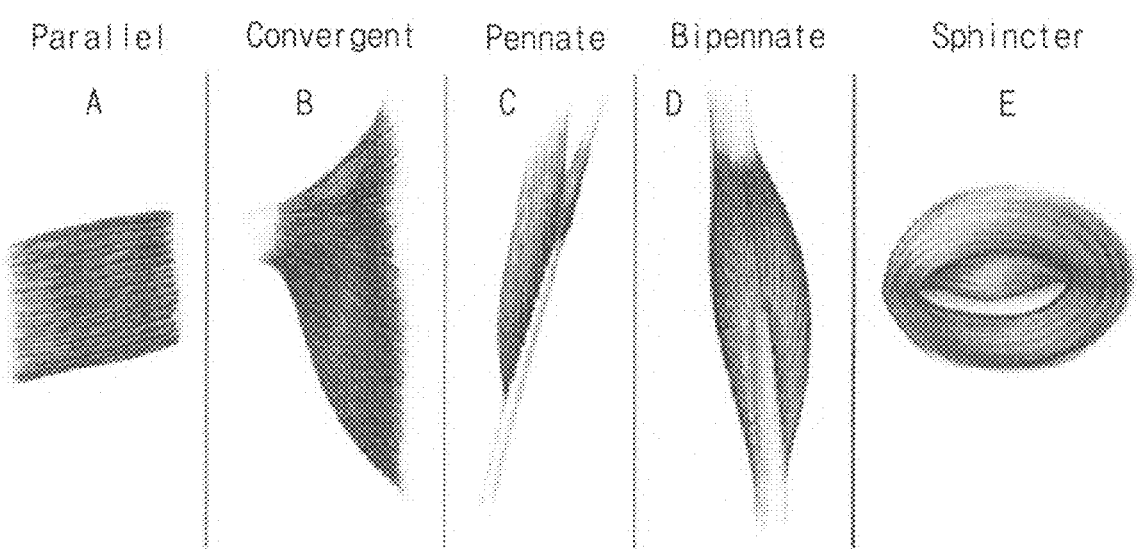
FIG. 1B is a schematic view illustrating representative forms of the muscle-tendon unit in human beings or animals in FIG. 1A.
Figure 2:
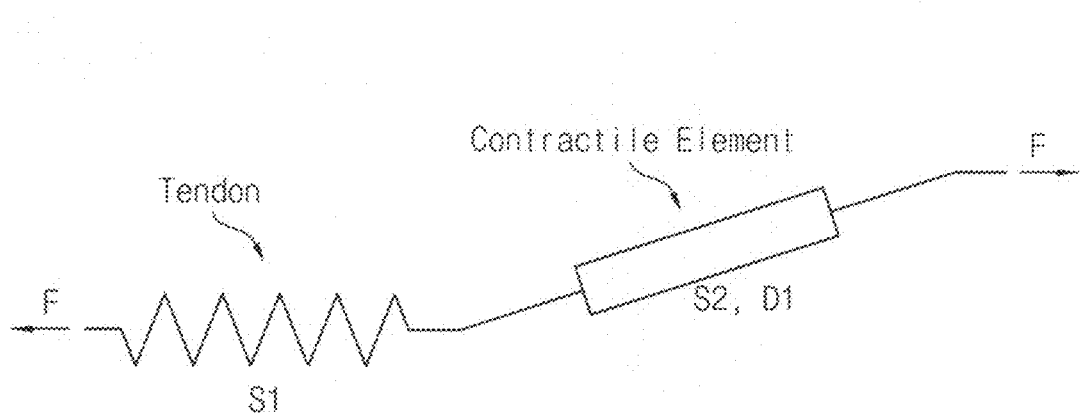
FIG. 2 is a schematic view illustrating Hill's muscle model modeling a macroscopic structure of the muscle-tendon unit.

FIG. 1A is a schematic view illustrating a muscle-tendon unit in human beings or animals. FIG. 1B is a schematic view illustrating representative forms of the muscle-tendon unit in human beings or animals in FIG. 1A. FIG. 2 is a schematic view illustrating Hill's muscle model modeling a macroscopic structure of the muscle-tendon unit.

Referring to FIGS. 1A and 1B, as in the structure of the muscle-tendon unit in human beings or animals, the movement of human beings or animals is performed via the muscle-tendon unit, and the structure of the muscle-tendon unit may be modeled macroscopically as Hill's muscle model as illustrated in FIG. 2.

Referring to FIG. 2, as an external force F is applied, the tendon elastically behaves as an elastic body S1, and the muscle behaves both as an elastic body S2 and a damper D1 at the same time.

Here, the tendon is the passive elastic component and the muscle is the active contractile component.

Further, at the muscle-tendon unit in human beings and animals, the tendon has golgi tendon organs sensing an applied tension, and the muscle has muscle spindles sensing a length change of the muscle.

Figure 3A:
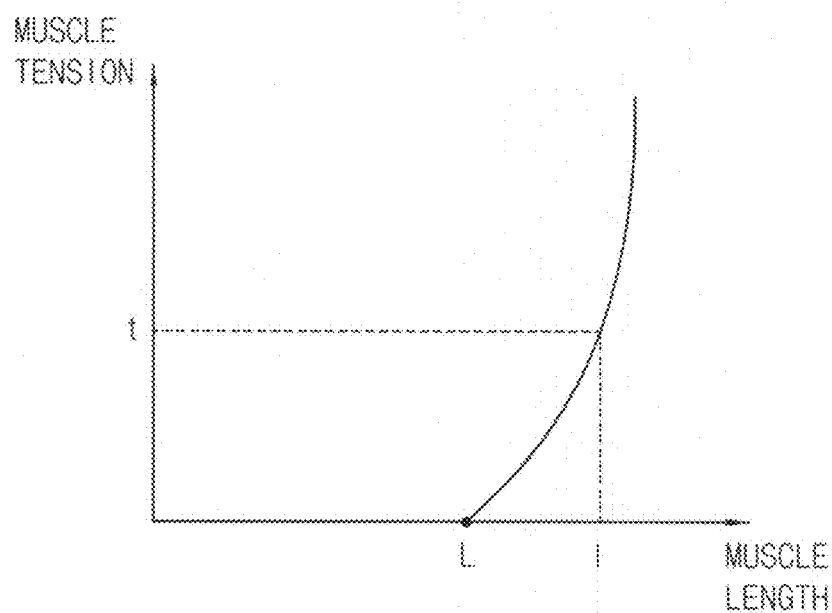
FIG. 3A is a graph illustrating a length-tension relationship of the muscle-tendon unit based on a controlled original muscle-tendon length L.
Figure 3B:
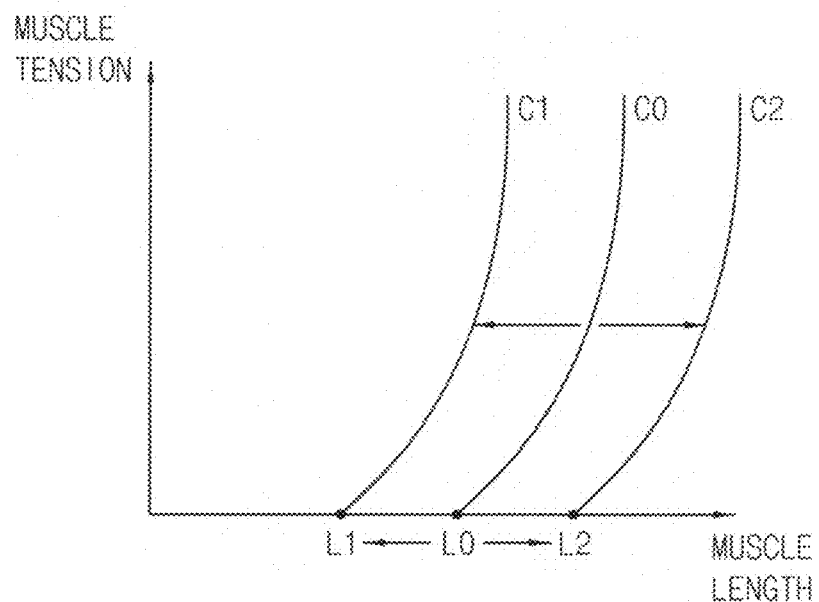
FIG. 3B is a graph illustrating the length-tension relationships of a muscle-tendon unit (C1, C0, and C2) at different original muscle-tendon lengths (L1, L0 and L2 respectively)

FIG. 3A is a graph illustrating a length-tension relationship of the muscle-tendon unit based on a controlled original muscle-tendon length L, and FIG. 3B is a graph illustrating the length-tension relationships of a muscle-tendon unit (C1, C0, and C2) at different original muscle-tendon lengths (L1, L0 and L2 respectively).

Referring to FIG. 3A, when the muscle-tendon unit is voluntarily controlled to a specific original length L, and an external force is applied to the muscle-tendon unit, the muscle tendon-unit will passively adjust the length and the tension based on the established length-tension relationship of the muscle-tendon unit.

When the external force disappears in the above case, the muscle-tendon unit returns back to its original the length L which is voluntarily controlled.

In addition, as illustrated in FIG. 3A, the length-tension relationship of the muscle-tendon unit may be linear or non-linear, and its characteristics depend on specific (gastrocnemius, hamstring, etc.) muscle-tendon unit.

Referring to FIG. 3B, the original muscle-tendon length may be voluntarily controlled variously such as L1, L0 and L2; however, since the muscle-tendon unit can voluntarily perform contraction or relaxation, an external force is necessary for lengthening contraction.

Accordingly, as explained referring to FIGS. 1A to 3B, the biological muscle-tendon contractions are performed based on voluntary control of the original muscle-tendon unit length, and its corresponding length-tension relationship. In addition, the original length of the muscle-tendon unit may be controlled both feed-forward and feedback manner depending on the task.

Although explained below, the biomimetic artificial muscle module and the biomimetic artificial muscle assembly, may mimic the contraction characteristics of the muscle-tendon unit in human beings or animals, more correctly and more effectively.

Figure 4:
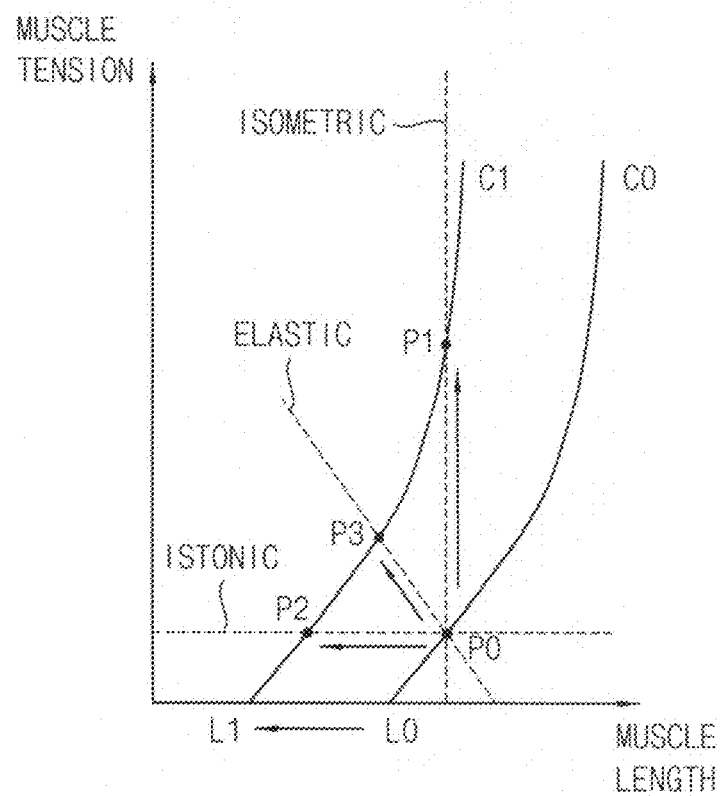
FIG. 4 is a graph illustrating the changes of the length and/or the tension of the muscle-tendon unit in isometric, isotonic, and elastic contraction based on the original muscle-tendon lengths controlled from L0 to L1 or L1 to L0.

FIG. 4 is a graph illustrating the changes of the length and/or the tension of the muscle-tendon unit in isometric, isotonic, and elastic contraction based on the original muscle-tendon lengths controlled from L0 to L1 or L1 to L0.

Hereinafter, the biological characteristics of muscle-tendon contractions are explained referring to FIG. 4.

Here, in the isometric contraction, total length of the muscle-tendon unit is maintained uniformly regardless of tension generated by the muscle-tendon unit. For example, when a waiter adds a dish on a plate supported by the waiter or removes the dish from the plate, the position of the plate is maintained even though the tension of the muscle-tendon unit is changed due to the increase or decrease of the weight of the dish on the plate.

In other words, total length of the muscle-tendon unit is maintained uniformly, even though the tension applied to the muscle-tendon unit is increased or decreased, which means that the position P0 is changed to the position P1 or the position P1 is changed back to the position P0, in FIG. 4.

In the isotonic contraction, the tension applied to the muscle-tendon unit is maintained uniformly but the length of the muscle-tendon unit is changed. For example, when the waiter lifts the plates up or down, the weight of the plate is constant and thus the tension of the muscle-tendon unit is maintained but the length of the muscle-tendon unit is decreased or increased with the lifting movement of the plates.

In other words, the tension applied to the muscle-tendon unit is maintained but total length of the muscle-tendon unit is decreased or increased, which means that the position P0 is changed to the position P2 or the position P2 is changed back to the position P0, in FIG. 4.

In the elastic contraction, the tension and the length of the muscle-tendon unit are changed at the same time. For example, when the waiter lifts up or down the plate with adding the dish on the plate or removing the dish from the plate, the tension and the length of the muscle-tendon unit are both changed.

In other words, the tension applied to the muscle-tension unit is changed and total length of the muscle-tendon unit is decreased or increased at the same time, which means that the position P0 is changed to the position P3 or the position P3 is changed back to the position P0, in FIG. 4.

In addition, FIG. 4, all muscle-tendon contractions (isometric, isotonic, and elastic) are performed base on voluntary control the original muscle length from L0 to L1 or L1 to L0, and its corresponding muscle length-tension relationship.

Thus, in FIG. 4, the voluntarily controlled original length L0, and L1 may be the control command for the muscle-tendon contractions.

Accordingly, the biological structures and control characteristics of the muscle-tendon unit mentioned above, may be mimicked by the biomimetic artificial muscle module and the biomimetic artificial muscle assembly according to the example embodiments mentioned below.

Hereinafter, the biomimetic artificial muscle module and the method of controlling the biomimetic artificial muscle module are explained for mimicking the characteristics of the muscle-tendon unit in human beings or animals mentioned above.

Figure 5:
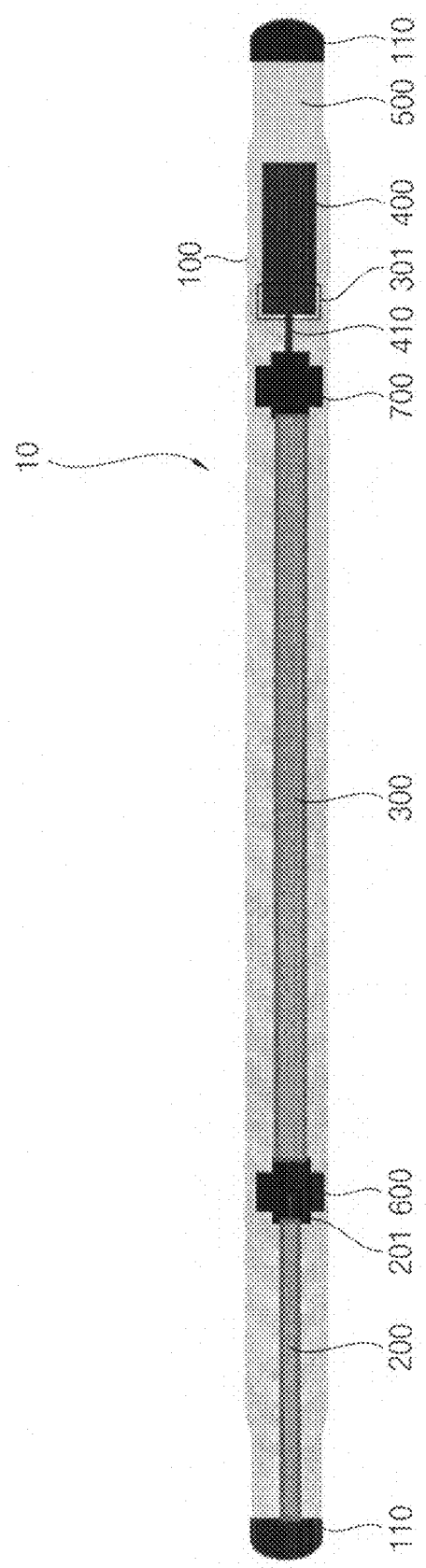
FIG. 5 is a schematic view illustrating a biomimetic artificial muscle module according to the present example embodiment of the present invention.

FIG. 5 is a schematic view illustrating a biomimetic artificial muscle module according to the present example embodiment of the present invention.

Referring to FIG. 5, the biomimetic artificial muscle module (hereinafter, artificial muscle module) includes an outer part 100, a cover 110, an elastic part 200, a first sensor 201, an operating part 300, a second sensor 301, a driving part 400, a driving transmitting part 410, a locking part 500, a first connector 600 and a second connector 700.

The outer part 100 forms an outer structure of the artificial muscle module 10, and for example may be bellows. The outer part 100 is formed similar to a real muscle-tendon tissue, and has flexibility.

The cover 110 is fixed to the outer part 100. The cover 110 connects and encloses elements at both ends of the outer part 100, and connects or fixes the elements to other elements such as musculoskeletal system or other modules.

Both ends of the outer part 100 are open, and the elements are disposed inside of the outer part 100. The both ends of the outer part 100 are enclosed by the cover 110, and thus the artificial muscle module 10 is formed.

A first end of the elastic part 200 is fixed to the cover 110, and a second end of the elastic part 200 is fixed to the first connector 600.

Here, a size and a structure of the cover 110 is not limited thereto, when the cover 110 connects and encloses the elements disposed at both ends of the artificial muscle module 10, and at the same time, connects the elements or fixes the elements to other elements such as musculoskeletal system or other modules.

The elastic part 200 has elastic behavior, and corresponds to tendon at a muscle-tendon unit of human beings or animals.

The elastic part 200 may be, for example, a spring, an elastic rubber, an elastic wire and so on, and may include various kinds of elastic materials.

The first sensor 201 measures physical quantity, such as a tension or a length of the elastic part 200, and the measured physical quantity may be calculated from each other using the measured value and conventionally defined values. Thus, various kinds of sensors may be used as the first sensor 201.

In addition, although the first sensor 201 is disposed at the first connector 600 in FIG. 5, the first sensor 201 may be disposed at any position where the physical quantity of the elastic part 200 is measured. Further, although not shown in the figure, the measured information may be transmitted to a main controller.

A first end of the operating part 300 is connected to the first connector 600, and a second end of the operating part 300 is connected to the second connector 700.

Here, the operating part 300 corresponds to the muscle at the muscle-tendon unit in human beings or animals, and thus the operating part 300 may be contracted or relaxed since the muscle of human beings or animals is only contracted or relaxed.

In addition, the operating part 300 may be, for example, a shape-memory alloy, a twisting wire, a thermal contraction tube, and so on, which can cause the change of the length of the operating part 300 due to rotation, length change, twisting or mixed contraction thereof, but not limited thereto.

The first connector 600 connects the operating part 300 with the elastic part 200, and moves linearly according to the change of the length of the elastic part 200 and the operating part 300.

Accordingly, the first connector 600 may be disposed at an arbitrary position in the outer part 100 according to the relative length of the elastic part 200 and the operating part 300.

As explained referring to FIGS. 3A and 3B, the biological muscle-tendon contractions for are performed based on the voluntary control the original muscle-tendon unit length and its tension-length relationship.

Accordingly, in the present example embodiment, the elastic part 200 and the operating part 300 satisfy the linear or non-linear tension-length relationship of the muscle-tendon unit, as illustrated in FIGS. 3A and 3B, and the length and tension are changes according to the applied external force.

The driving part 400 provides a driving force to the operating part 300 through the second connector 700.

Here, the driving part 400 only contracts or relaxes the operating part 300, and thus, the operating part 300 may not be lengthened without the external force.

The driving part 400 may be based on, for example, a pneumatic driving, an electric field driving, a thermal driving, a mechanical driving and so on, and at least one of the driving mechanisms may be selected considering the operating part 300.

For example, when the operating part 300 is the twisting wire, the driving part 400 may be a motor based on the mechanical driving. When the operating part 300 is the thermal contraction tube, the driving part 400 may be a thermal driving unit based on the thermal driving.

In the present example embodiment, for the convenience of explanation, the driving part 400 is distinct from the operating part 300, but the driving part 400 is included in the operating part 300 and is integrally formed with the operating part 300. Here, when the driving part 400 is included in and is integrally formed with the operating part 300, the driving transmitting part 410 is also included in and is integrally formed with the operating part 300.

The second sensor 301 is equipped to the driving part 400, and measures the driving quantity of the driving part 400. Here, the driving quantity of the driving part 400 is an amount of driving of the driving part 400, and may be, for example, an amount of rotation of the driving part 400. When the rotation of the driving part 400 is measured, the length of the operating part 300 is changed in proportion to the amount of rotation of the driving part 400, and thus, contracted length of the operating part 300 may be finally calculated.

In addition, although not shown in the figure, the second sensor 301 may directly measure the physical quantity of the operating part 300, such as the tension, the length and so on, and the measured physical quantity may be calculated from each other using the measured value and conventionally defined value. Thus, various kinds of sensors may be used as the second sensor 301.

In addition, the position of the second sensor 301 is not limited when the physical quantity of the operating part 300 such as the tension, the length and so on is measured.

The information measured in the second sensor 301 may be provided to the main controller (not shown).

Although not shown in the figure, the main controller controls the driving part 400, based on the information from the first and second sensors 201 and 301.

Here, the main controller may be equipped inside or outside of the outer part 100.

Although not shown in the figure, the artificial muscle module according to the present example embodiment may be divided into sub modules like an artificial muscle elastic module including the elastic part and the first sensor and an artificial muscle operating module including the operating part, the driving part, the locking part, the second connector and the second sensor.

Here, each of the artificial muscle elastic module and the artificial muscle operating module may include the outer part and the cover.

Here, the first connector may be replaced by the cover of the artificial muscle elastic module and the artificial muscle operating module, and thus the first connector is unnecessary.

Figure 6:
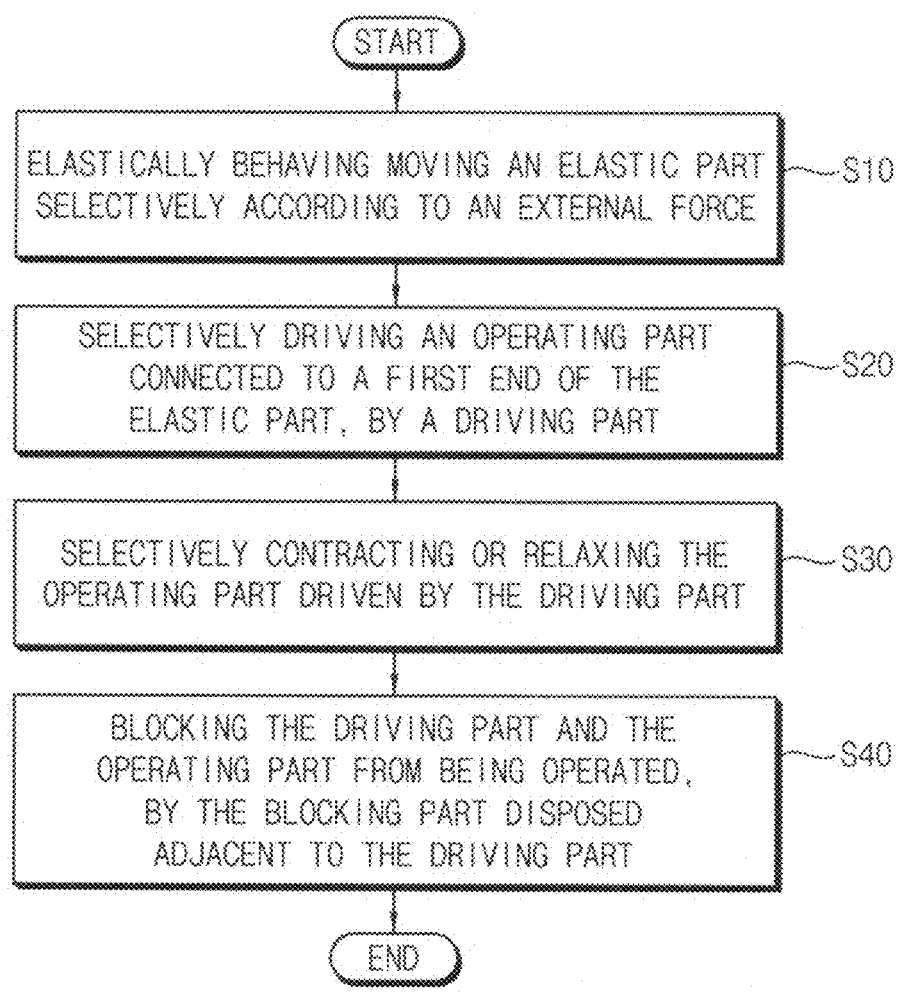
FIG. 6 is a flow chart showing a method of controlling the biomimetic artificial muscle module of FIG. 5.

FIG. 6 is a flow chart showing a method of controlling the biomimetic artificial muscle module of FIG. 5.

Referring to FIG. 6, the method of controlling the artificial muscle module is explained below.

In FIG. 6, the steps are illustrated for the understandings, but each of the steps in FIG. 6 may be changed or performed at the same time.

First, the elastic part 200 is elastically behaves according to an external force applied thereto (step S10).

Here, when the external force is same as the previous external force, the length of the elastic part 200 is maintained uniformly. Alternatively, when the external force is increased or decreased compared to the previous external force, the length and the tension of the elastic part 200 is increased or decreased.

Then, when the length of the elastic part 200 is increased or decreased, the driving part 400 selectively provides the driving force to the operating part 300 (step S20).

Here, as the elastic behavior of the elastic part 200, the driving part 400 selectively provides the driving force to the operating part 300, considering whether total length of the artificial muscle module 10 is need to be maintained or changed.

Then, when the driving part 400 is selectively driven according as total length of the artificial muscle module 10 is maintained or changed, the length of the operating part 300 is controlled, and the further explanation will be explained below (step S30).

Then, the locking part 500 selectively blocks the operating part 300 from being operated (step S40).

The locking part 500 is in the locking state to block the operating part 300 from being operated, when the contraction or relaxation of the operating part 300 is finished or the contraction or relaxation of the operating part 300 is to be limited.

Hereinafter, three different types of muscle-tendon contractions in human beings or animals are mimicked by the artificial muscle module 10, and the operation of its parts is explained.

Figure 7:
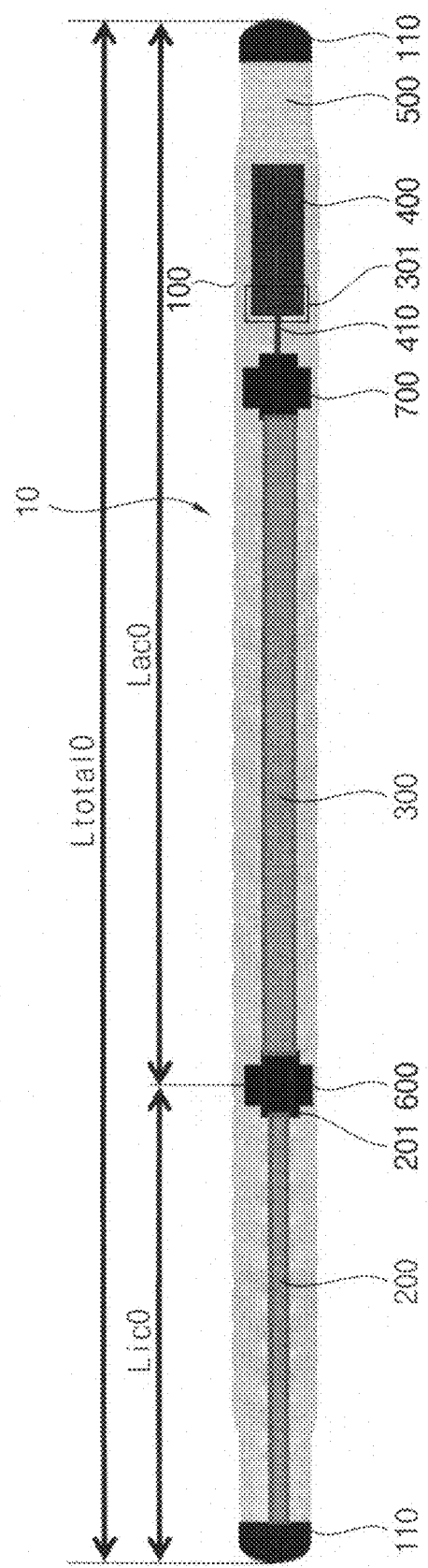
FIGS. 7 to 9 are schematic views illustrating example controls of the biomimetic artificial muscle module of FIG. 5.
Figure 8:
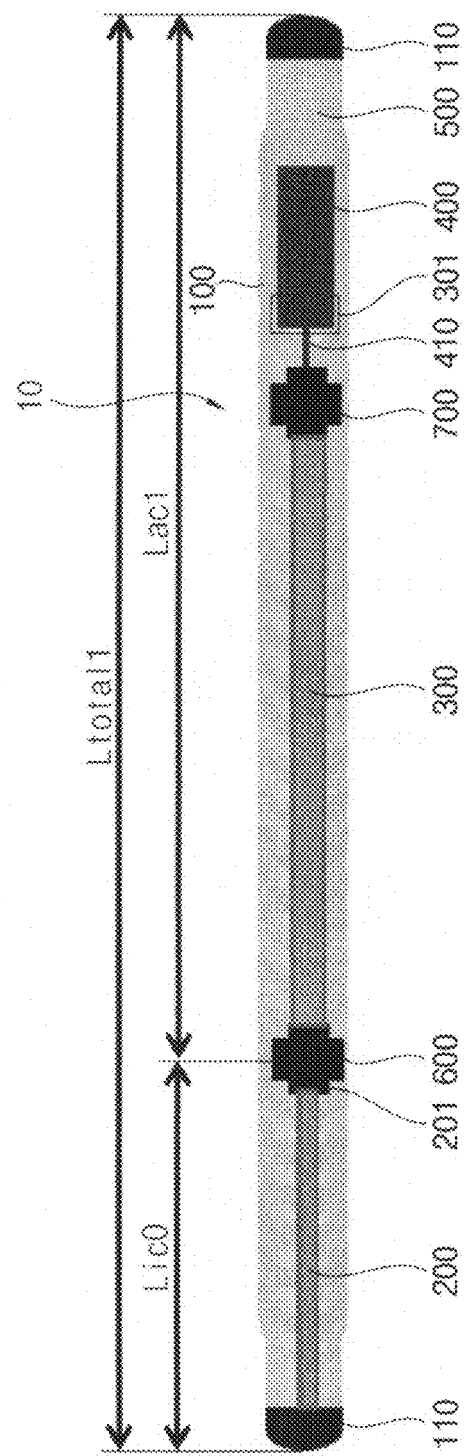
Figure 9:
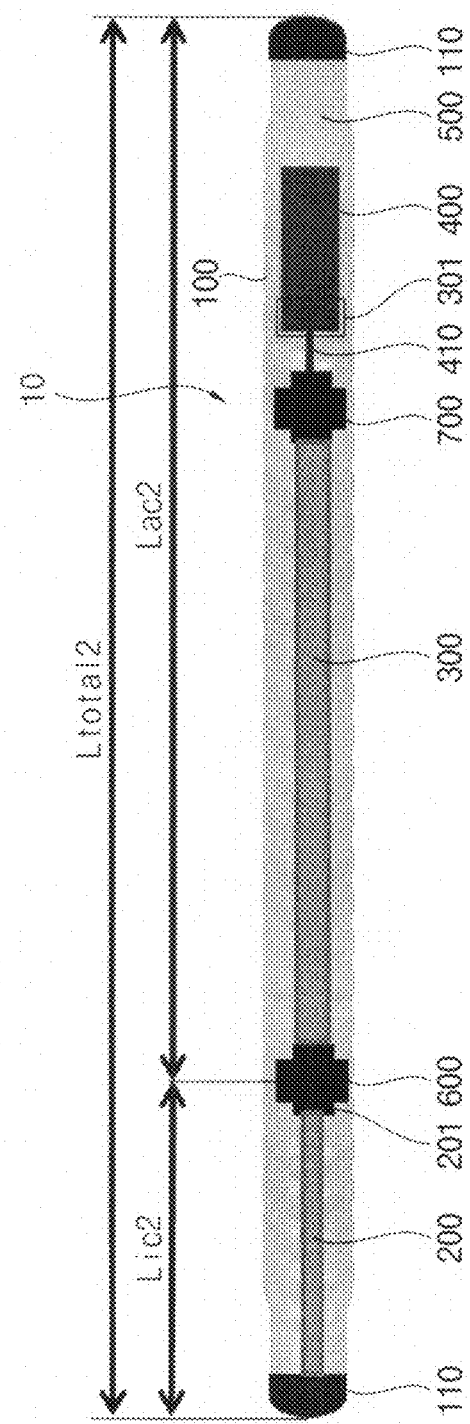

FIGS. 7 to 9 are schematic views illustrating example controls of the biomimetic artificial muscle module of FIG. 5.

Referring to FIG. 7, the artificial muscle module mimics the isometric contraction, as explained referring to FIG. 4.

As illustrated in FIG. 7, total length of the artificial muscle module 10 is assumed to be Ltotal0, a length of the elastic part 200 is assumed to be Lic0, and a length of the operating part 300 is assumed to be Lac0. Here, the length of the elastic part 200 is substantially smaller than Lic0 (Lic0 includes the cover 110 and the first connector 600), and the length of the operating part 300 is substantially smaller than Lac0 (Lac0 includes the second connector 700, the driving transmitting part 410, the driving part 400 and the locking part 500), but the length of the elastic part and the length of the operating part are only changed, and thus the above assumption may be reasonable.

Here, total length of the artificial muscle module 10 is maintained uniformly in the isometric contraction, and thus the length of the contraction or relaxation of the operating part 300 may be controlled considering the increasing or decreasing length of the elastic part 200. Thus, the operating part 300 is contracted or relaxed substantially same as the increasing or decreasing length of the elastic part 200, so that total length of the artificial muscle module 10 may be maintained uniformly with an initial length thereof (Ltotal0→Ltotal0).

Accordingly, even though the external force is increased or decreased, the total length of the artificial muscle module 10 uniformly maintained, and thus the isometric contraction may be mimicked.

Referring to FIG. 8, the artificial muscle module 10 mimics the isotonic contraction, as explained referring to FIG. 4.

In the isotonic contraction, as explained above, the length of the muscle unit is changed with maintaining the tension uniformly.

When the artificial muscle module 10 mimics the isotonic contraction, the external force applied to the artificial muscle module 10 is maintained uniformly so that the length of the elastic part 200 does not change, while the length of the artificial muscle module 10 is changed.

To mimic the isotonic contraction, referring to FIGS. 6 and 8, in the step S10, the length of the elastic part 200 is maintained uniformly (Lic0→Lic0) since the external force is maintained uniformly.

In addition, in the step S20 and the step S30, the driving part 400 drives the operating part 300, and the operating part 300 is contracted or relaxed and the length of the operating part 300 is changed (Lac0→Lac1).

Thus, total length of the artificial muscle module 10 is changed (Ltotal0→Ltotal1) with the tension of the artificial muscle module uniformly maintained. Thus, the isotonic contraction may be mimicked.

Referring to FIG. 9, the artificial muscle module 10 mimics the elastic contraction, as explained referring to FIG. 4.

In the elastic contraction, as explained above, the length of the muscle and the tension are both changed.

When the artificial muscle module 10 mimics the elastic contraction, the external force applied to the artificial muscle module 10 is changed, and the length of the artificial muscle module 10 is changed at the same time.

To mimic the elastic contraction, referring to FIGS. 6 and 9, in the step S10, when the external force is increased or decreased, the length and the tension of the elastic part 200 is increased or decreased (Lic0→Lic2).

In addition, in the step S20 and the step S30, the driving part 400 drives the operating part 300, and thus the operating part 300 is contracted or relaxed so that the length of the operating part 300 is changed (Lac0→Lac2).

Here, total length of the artificial muscle module 10 is changed as the sum of the length change of the elastic part 200 and the length change of the operating part 300 (Ltotal0→Ltotal2).

Thus, total length and tension of the artificial muscle module 10 is changed at the same time, and thus the elastic contraction may be mimicked.

Although not included in the structure, the function and the control for the muscle-tendon unit of human beings or animals, the artificial muscle module 10 includes the locking part 500 so that the operating part 300 is selectively blocked when the elastic contraction of the muscle-tendon unit does not need to be considered. Thus, the energy necessary to maintain the length of the operating part 300 uniformly may be reduced or blocked.

Accordingly, the artificial muscle module explained referring to FIG. 5, may correctly and effectively mimic the isometric, the isotonic and the elastic contraction performed by the muscle-tendon unit of human beings or animals, via the method of controlling the artificial muscle module explained referring to FIG. 6.

Figure 10:
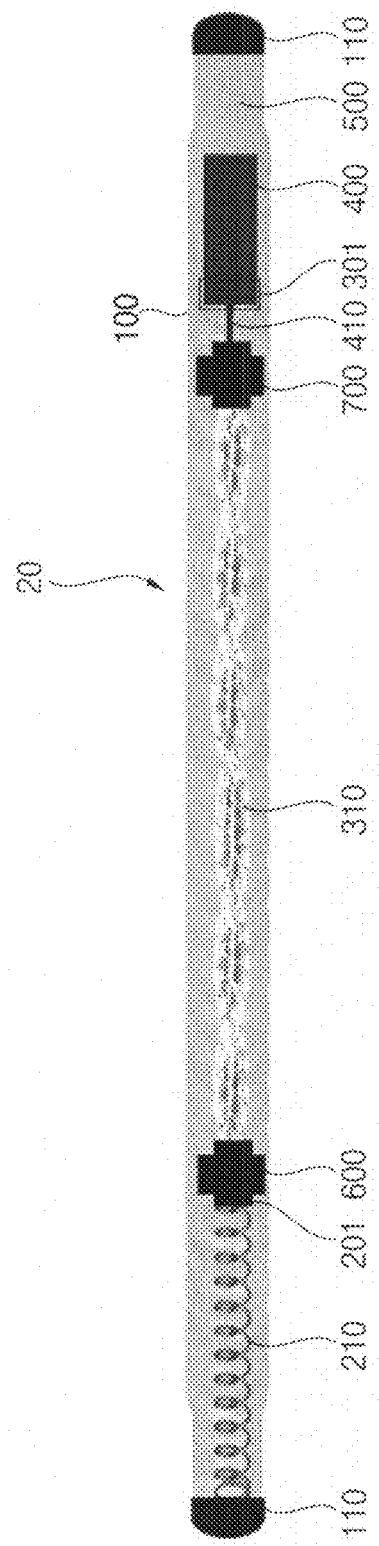
FIG. 10 is a schematic view illustrating a biomimetic artificial muscle module according to another example embodiment of the present invention.

FIG. 10 is a schematic view illustrating a biomimetic artificial muscle module according to another example embodiment of the present invention.

Referring to FIG. 10, in the artificial muscle module 20 according to the present example embodiment, an elastic part 210 includes a spring, an operating part 310 includes a twisting wire, and a driving part 400 includes a rotational motor. Thus, the artificial muscle module 20 is substantially same as the artificial muscle module 10 according to the previous example embodiment in FIG. 5.

Further, a method of controlling the artificial muscle module 20 is substantially same as the method explained referring to FIGS. 6 to 9, and thus the isometric contraction, the isotonic contraction and the elastic contraction are mimicked correctly and effectively.

FIG. 11A to 11E are schematic views illustrating a biomimetic artificial muscle assembly having the biomimetic artificial muscle modules of the previous example embodiments.

Figure 11A:
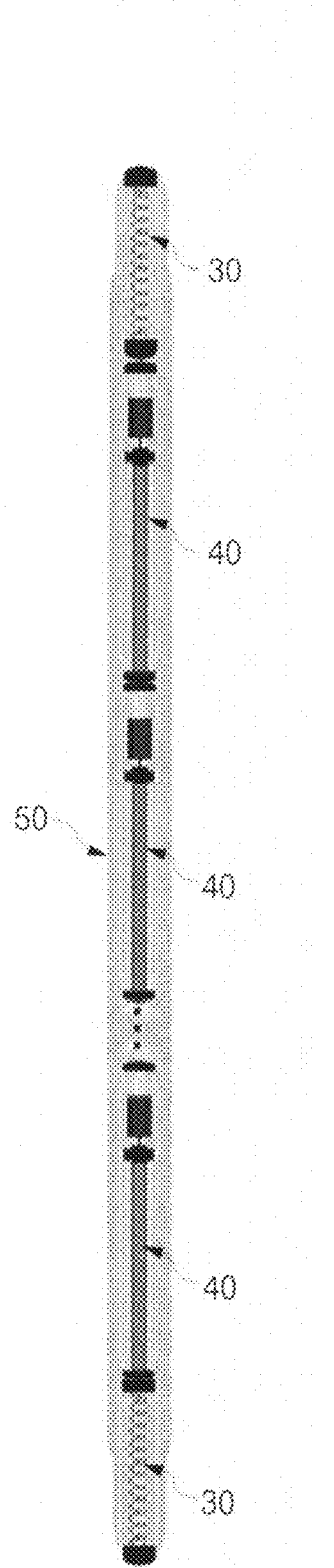
FIG. 11A to 11E are schematic views illustrating a biomimetic artificial muscle assembly having the biomimetic artificial muscle modules of the previous example embodiments.

Referring to FIG. 11A, the artificial muscle assembly 50 includes an artificial muscle operating module 40 and an artificial muscle elastic module 30. At least one artificial muscle operating modules 40 are connected in series along a direction, and the artificial muscle elastic module 30 is connected to one end or both ends of the series of artificial muscle operating modules 40. Here, the operation of the artificial muscle assembly 50 is substantially same as the artificial muscle module explained above, and each of the artificial muscle operating modules 40 may be independently or simultaneously driven.

Figure 11B:
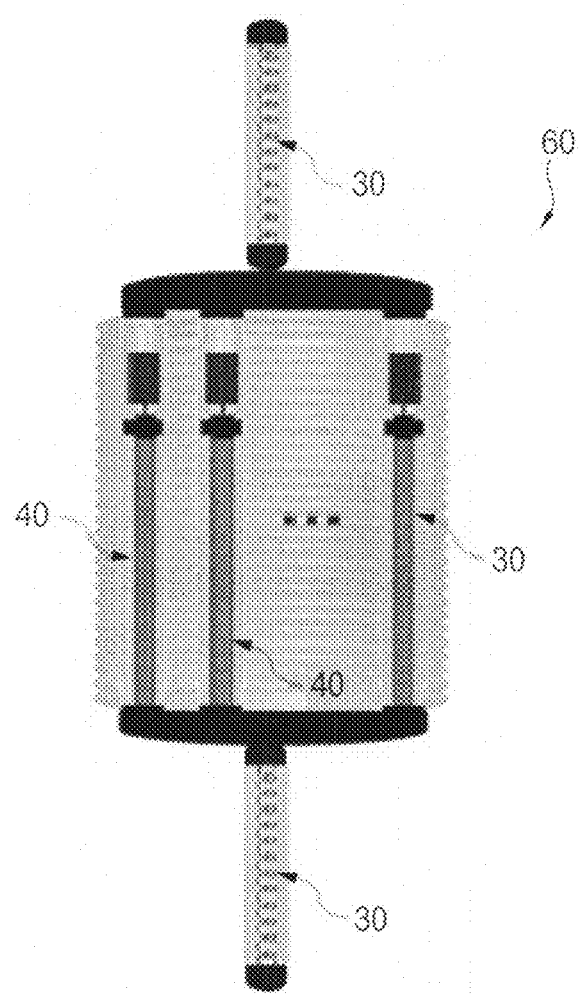

Referring to FIG. 11B, at least one artificial muscle operating modules 40 are connected in parallel, to form an artificial muscle assembly 60.

Figure 11C:
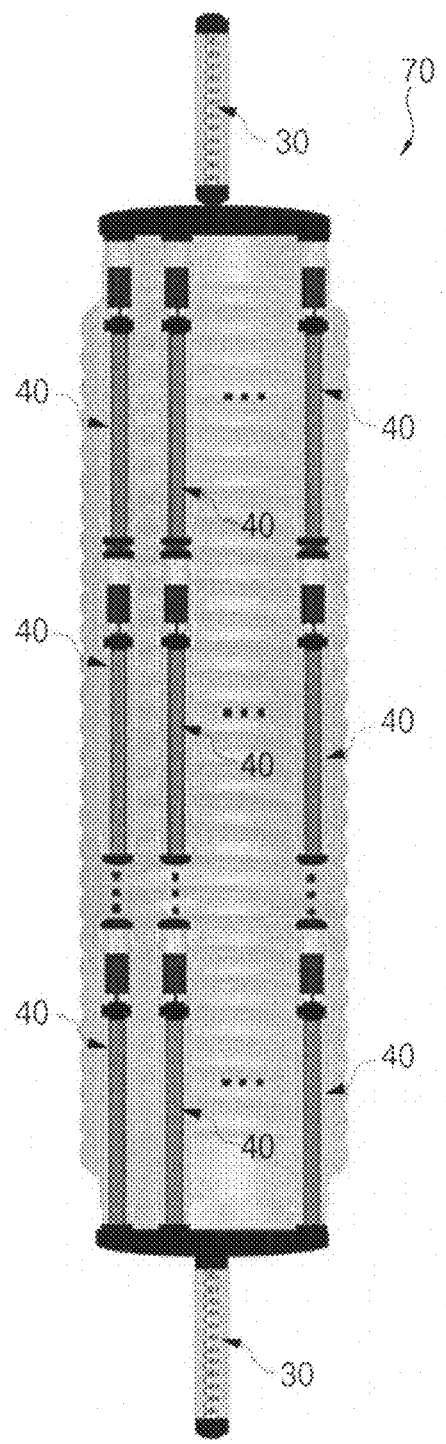

Referring to FIG. 11C, at least one artificial muscle operating modules 40 are connected in parallel and at least two artificial muscle operating modules 40 are connected in series, to form an artificial muscle assembly 70.

Figure 11D:
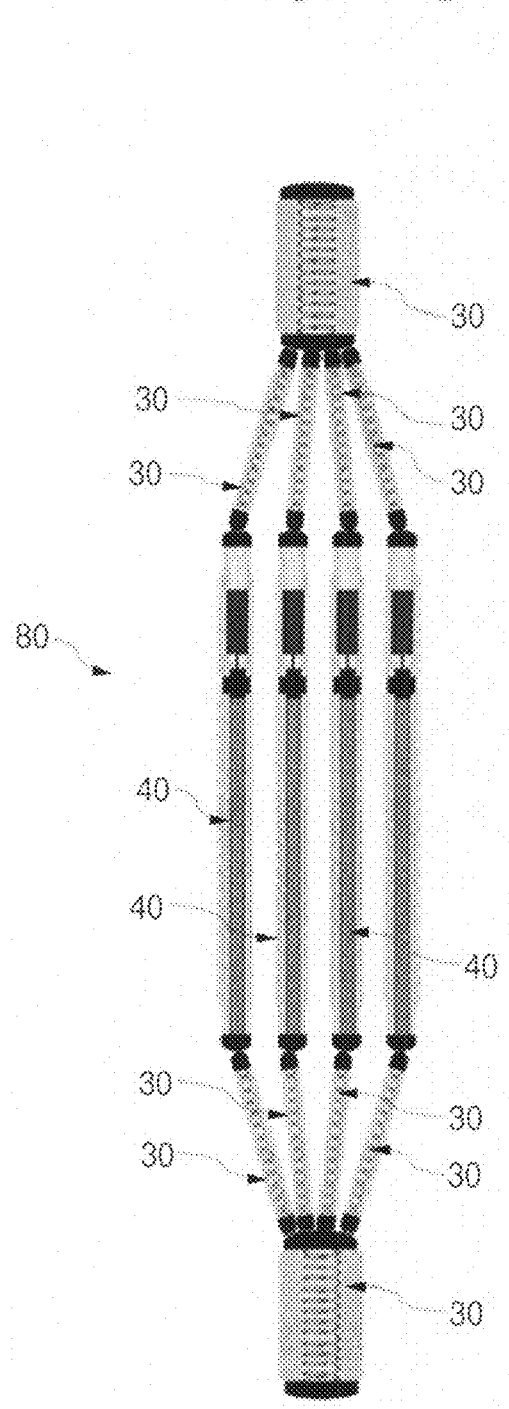
Figure 11E:
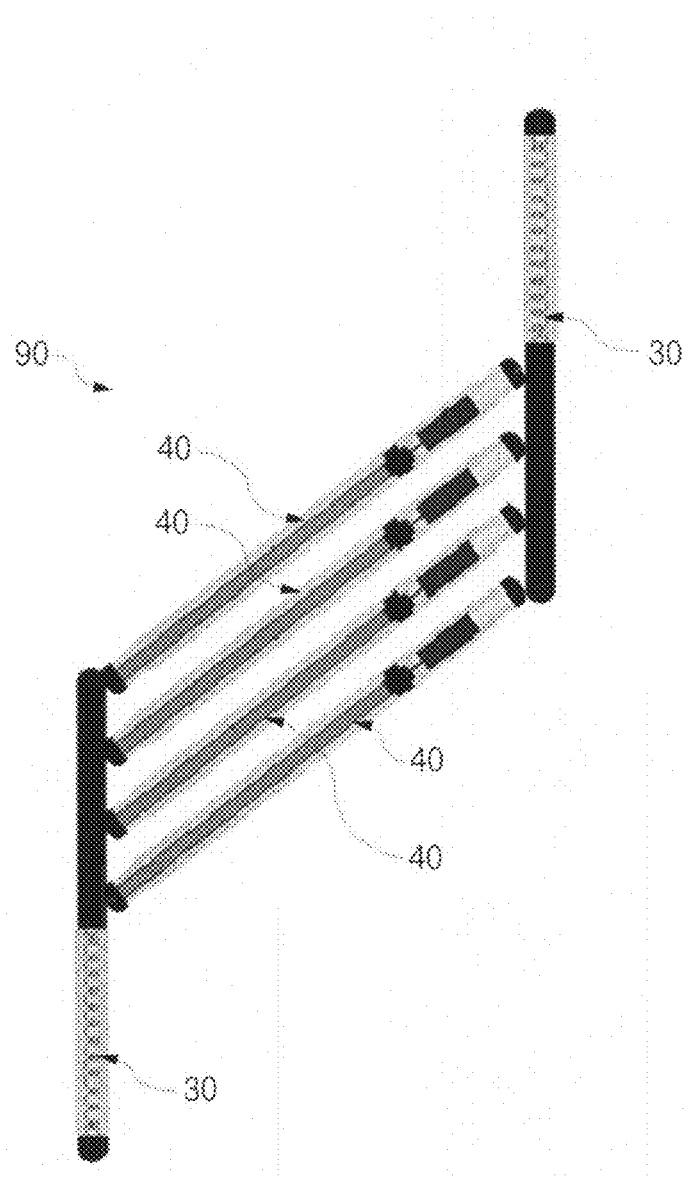

Referring to FIGS. 11D and 11E, the artificial muscle elastic module 30 and the artificial muscle operating module 40 are connected in parallel, in series or in an arbitrary arrangement, to mimic the form of the muscle-tendon unit of human beings or animals.

The operation of the artificial muscle assembly in FIGS. 11A to 11E, is substantially same as the artificial muscle module, and each of the artificial muscle operating modules 40 may be independently or simultaneously driven.

In addition, although not shown in the figure, the artificial muscle assembly may include the artificial muscle elastic module and the artificial muscle operating module which have the size and the applied mechanism different from each other and are arranged in a two-dimensional plane or in a three-dimensional space with a geometrical or natural arrangement.

Accordingly, the artificial muscle assembly may mimic the structure, the function and the control of the muscle-tendon unit of human beings or animals, more specifically.

According to the present example embodiments, biological characteristics of muscle-tendon contraction in human beings or animals may be easily mimicked with relatively simple structure and control method.

The operating part is merely controlled to be contracted or relaxed, such that the motion of muscle-tendon unit may be mimicked. Thus, the control may be simplified for the simulation more correctly.

In addition, since the biomimetic artificial muscle module includes only a few components with simple structure, miniaturization and modularization may be achieved and thus may be applied to various applications.

In addition, various kinds of materials, structures, and designs may be applied to the elastic part, and various kinds of mechanism, structures, functions and designs may be applied to the driving part and the operating part.

In addition, due to the capability of miniaturization and modularization, the biomimetic artificial muscle assembly having a plurality of modules may be constructed, so that the various shapes of muscle-tendon unit and its functional characteristics in human beings may be mimicked more precisely.

In addition, the biomimetic artificial muscle module and biomimetic artificial muscle assembly may mimic the contraction characteristics of human or animal muscle-tendon unit more correctly and effectively by its design and control method.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. An artificial muscle module comprising:
   an operating part contracting or relaxing along a longitudinal direction of the artificial muscle module and having first and second ends opposing each other in the longitudinal direction;

an elastic part connected to the first end of the operating part, and behaving elastically according to an external force;

a driving part connected to the second end of the operating part, and driving the operating part to be contracted or relaxed; and first and second sensors respectively sensing the elastic part and the operating part, wherein a length of the operating part is selectively prevented from being changed in the longitudinal direction.

2. The artificial muscle module of claim 1, further comprising:

a driving transmitting part configured for transmitting the driving of the driving part to the operating part.

3. The artificial muscle module of claim 2, further comprising:

a first connector connecting the elastic part with the operating part; and a second connector connecting the operating part with the driving transmitting part.

4. The artificial muscle module of claim 3, wherein the driving part, the operating part, the driving transmitting part and the second connector are integrally formed with each other.

5. The artificial muscle module of claim 2, further comprising:

an outer part forming an outer structure of the artificial muscle module; and a cover enclosing elements inside of the outer part, and connecting the elements to outer elements.

6. The artificial muscle module of claim 1, wherein the first sensor is configured to measure a length or a tension of the elastic part, and the second sensor is configured to measure (i) driving amount of the driving part and/or (ii) a length or a tension of the operating part to calculate driving amount, a length, a tension, a velocity and an acceleration of the artificial muscle module.

7. The artificial muscle module of claim 1, wherein the elastic part is one of a spring, an elastic rubber and an elastic wire, wherein the operating part is one of shape-memory alloys, a twisting wire/fiber and a thermal contraction tube, and wherein the driving part is driven via one of pneumatic driving, electric field driving, thermal driving and mechanical driving.

8. The artificial muscle module of claim 1, wherein the driving part and the operating part are configured to be blocked from being operated to minimize energy consumption, when elastic behavior of the muscle-tendon unit is unnecessary to be considered.

9. The artificial muscle module of claim 1, wherein in mimicking isometric contraction, a length of the elastic part is increased or decreased, a length of the operating part is decreased or increased, and thus total length of the artificial muscle module is maintained.

10. The artificial muscle module of claim 1, wherein in mimicking isotonic contraction, a length of the elastic part is maintained, a length of the operating part is decreased or increased, and thus total length of the artificial muscle module is decreased or increased.

11. The artificial muscle module of claim 1, wherein in mimicking elastic contraction, a length of the elastic part is decreased or increased, a length of the operating part is decreased o increased, and thus total length of the artificial muscle module is decreased or increased due to the sum of length change of the elastic part and the operating part.

12. A method of controlling an artificial muscle module, the method comprising:

elastically behaving an elastic part selectively according to an external force;

selectively driving an operating part by a driving part, wherein the operating part has first and second ends opposing each other in the longitudinal direction, the elastic part connected to the first end of the operating part and the driving part connected to the second end of the operating part;

selectively contracting or relaxing the operating part driven by the driving part both feed-forward and feedback manner depending on a task to control an original length of an operating part; and blocking the driving part and the operating part from being operated.

13. An artificial muscle assembly comprising:

an artificial muscle elastic module and an artificial muscle operating module, wherein the artificial muscle elastic module comprises:

an elastic part behaving elastically according to an external force; and a first sensor sensing the elastic part, wherein the artificial muscle operating module comprises:

an operating part contracting or relaxing along a longitudinal direction, the operating part having first and second ends opposing each other in the longitudinal direction, the first end of the operating part connected to the elastic part;

a driving part connected to the second end of the operating part, and driving the operating part to be contracted or relaxed; and a second sensor sensing the operating part or the driving part, wherein a length of the operating part is selectively prevented from being changed in the longitudinal direction.

14. The artificial muscle assembly of claim 13, wherein a plurality of the artificial muscle elastic modules is connected, continuously in series, in parallel with each other, or serially and in parallel, wherein a plurality of the artificial muscle operating modules is connected, continuously in series, in parallel with each other, or serially and in parallel, wherein the artificial muscle elastic module is connected to at least one artificial muscle operating modules.

15. The artificial muscle assembly of claim 13, wherein an outer part and a cover are formed at each of the artificial muscle elastic module and the artificial muscle operating module.

16. The artificial muscle assembly of claim 13, wherein the driving part and the operating part are configured to be blocked from being operated to minimize energy consumption, when elastic behavior of the muscle-tendon unit is unnecessary to be considered.

17. The artificial muscle assembly of claim 13, wherein in mimicking isometric contraction, a length of the artificial muscle elastic module is increased or decreased, a length of the artificial muscle operating module is decreased or increased, and thus total length of the artificial muscle assembly is maintained.

18. The artificial muscle assembly of claim 13, wherein in mimicking isotonic contraction, a length of the artificial muscle elastic module is maintained, a length of the artificial muscle operating module is decreased or increased, and thus total length of the artificial muscle assembly is decreased or increased.

19. The artificial muscle assembly of claim 13, wherein in mimicking elastic contraction, a length of the artificial muscle elastic module is decreased or increased, a length of the artificial muscle operating module is decreased or increased, and thus total length of the artificial muscle assembly is decreased or increased due to the sum of length change of the artificial muscle elastic module and the artificial muscle operating module.

20. A method of controlling an artificial muscle assembly including an artificial muscle elastic module and an artificial muscle operating module, the method comprising:
- elastically behaving an elastic part of the artificial muscle elastic module selectively according to an external force;
- selectively driving an operating part of the artificial muscle operating module by a driving part of the artificial muscle operating module, the operating part having first and second ends opposing each other in the longitudinal direction, wherein the first end of the operating part is connected to the elastic part of the artificial muscle elastic module, and the second end of the operating part is connected to the driving part of the artificial muscle operating module;
- selectively contracting or relaxing the artificial muscle operating module driven by the driving part both feedforward and feedback manner depending on a task to control an original length of an operating part; and
- blocking the artificial muscle operating module from being operated.

* * * * *